US006995139B2

(12) United States Patent
Wenger et al.

(10) Patent No.: US 6,995,139 B2
(45) Date of Patent: Feb. 7, 2006

(54) CYCLIC UNDECAPEPTIDE PRO-DRUGS AND USES THEREOF

(75) Inventors: Roland Wenger, Riehen (CH); Manfred Mutter, Belmont-sur-Lausanne (CH); Amaud Hamel, Lausanne (CH); Francis Hubler, Rheinfelden (CH)

(73) Assignee: Debiopharm S.A., Lausanne (CH)

( * ) Notice: Subject to any disclaimer, the term of this patent is extended or adjusted under 35 U.S.C. 154(b) by 0 days.

(21) Appl. No.: 10/474,396

(22) PCT Filed: Apr. 22, 2002

(86) PCT No.: PCT/CH02/00222

§ 371 (c)(1),
(2), (4) Date: Oct. 9, 2003

(87) PCT Pub. No.: WO02/085928

PCT Pub. Date: Oct. 31, 2002

(65) Prior Publication Data

US 2004/0138108 A1    Jul. 15, 2004

(30) Foreign Application Priority Data

Apr. 20, 2001  (CH) .................................. 720/01

(51) Int. Cl.
*A61K 38/12* (2006.01)
*A61K 38/08* (2006.01)
*C07K 7/04* (2006.01)

(52) U.S. Cl. ................ 514/9; 514/2; 514/15; 530/300; 530/317; 530/321; 530/327; 530/345
(58) Field of Classification Search .............. 514/2, 514/9, 15; 530/300, 327, 321, 317, 345
See application file for complete search history.

(56) References Cited

U.S. PATENT DOCUMENTS

| | | | | |
|---|---|---|---|---|
| 4,396,542 A | * | 8/1983 | Wenger | 530/321 |
| 4,554,351 A | * | 11/1985 | Wenger | 544/177 |
| 4,639,439 A | * | 1/1987 | Howie et al. | 514/171 |
| 4,764,503 A | * | 8/1988 | Wenger | 514/11 |
| 5,169,773 A | * | 12/1992 | Rosenthaler et al. | 435/345 |
| 5,767,069 A | * | 6/1998 | Ko et al. | 514/11 |
| 5,981,479 A | * | 11/1999 | Ko et al. | 514/11 |
| 6,017,879 A | * | 1/2000 | Mutter et al. | 514/11 |
| 6,187,547 B1 | * | 2/2001 | Legay et al. | 435/7.1 |
| 6,204,257 B1 | * | 3/2001 | Stella et al. | 514/130 |
| 6,255,100 B1 | * | 7/2001 | Ko et al. | 435/254.11 |
| 6,274,629 B1 | * | 8/2001 | Cottens et al. | 514/646 |
| 6,288,029 B1 | * | 9/2001 | Mutter et al. | 514/9 |
| 6,486,209 B2 | * | 11/2002 | Cottens et al. | 514/646 |
| 6,765,019 B1 | * | 7/2004 | Crooks et al. | 514/529 |
| 6,790,935 B1 | * | 9/2004 | Mutter et al. | 530/317 |

FOREIGN PATENT DOCUMENTS

| | | |
|---|---|---|
| WO | WO 00/01715 | 1/2000 |
| WO | WO 200008033 A1 * | 2/2000 |
| WO | WO 200067801 A2 * | 11/2000 |
| WO | WO 200105818 A1 * | 1/2001 |
| WO | WO 200105819 A1 * | 1/2001 |
| WO | WO 01/13957 | 3/2001 |

OTHER PUBLICATIONS

Robert et al, "Collyre á la cyclosporine A: fabrication, toxicité, pharmacocinétique et indications in I'an 2000", J. Fr. Opthalmol., 2001, 24(5), pp. 527-535.

* cited by examiner

*Primary Examiner*—Bruce R. Campbell
*Assistant Examiner*—Andrew D. Kosar
(74) *Attorney, Agent, or Firm*—Nixon & Vanderhye P.C.

(57) ABSTRACT

A pro-drug comprising a cyclic undecapeptide wherein the peptide chain thereof comprises at least one amino acid residue, useful as a medicinal product, including use for treatment of pathological conditions of the eye.

15 Claims, 3 Drawing Sheets

CYCLIC UNDECAPEPTIDE PRO-DRUGS AND USES THEREOF

This application is the U.S. national phase of international application PCT/CH02/00222 filed 22 Apr. 2002, which designated the U.S. PCT/CH02/00222 claims priority of Switzerland Application No. 720/01 filed 20 Apr. 2001. The entire contents of these application are incorporated herein by reference.

The present invention relates to a pro-drug consisting of a cyclic undecapeptide and to the use thereof as a medicinal product, intended in particular for the treatment of pathological conditions of the eye.

Cyclosporins constitute a structurally distinct class of cyclic peptides which have in common the fact that they consist of a chain of eleven amino acids, some being atypical either due to their D configuration or due to the complex chemical structure of their side chain, or else due to the fact that the amine group is alkylated.

To date, about thirty cyclosporins have been isolated from a fungal source and many cyclic undecapeptides similar to these natural products have been obtained by hemisynthesis or by total synthesis. Also included among these cyclic undecapeptide analogs are peptolides or depsipeptides, i.e. cyclic polypeptides also containing ester linkages in their chain.

In the remainder of this description, and unless otherwise specified, the term "cyclosporin" will be intended to mean both the cyclic undecapeptides obtained from a natural source and their analogs obtained by hemisynthesis or total synthesis, including the peptolides obtained from a natural source or their analogues obtained by hemisynthesis or by total synthesis.

The first member of this cyclosporin family to have been isolated and then identified was Cyclosporin A. The peptide chain constituting its undecapeptide ring is as follows:
-MeBmt-Abu-Sar-MeLeu-Val-MeLeu-Ala-(D)Ala-MeLeu-MeLeu-MeVal- Its expanded chemical structure being as follows:

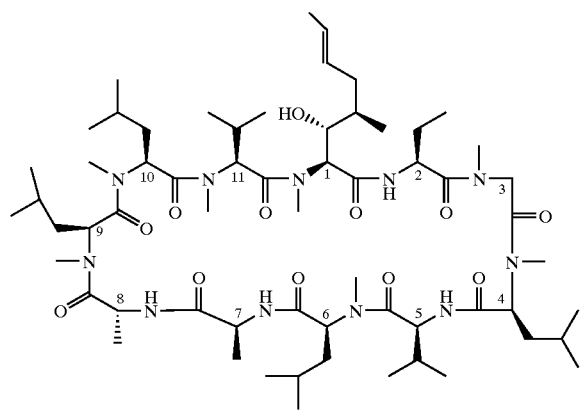

Cyclosporin A

Among the atypical amino acids which this cyclic undecapeptide comprises, that which is in the 1-position, namely N-methyl-(4R)-4-((E)-2-butenyl)-4-methyl-L-threonine, called MeBmt, is in particular noted.

This amino acid is specific to cyclosporins, it being possible for the ethylenic group to be optionally reduced. It has an amine group which is methylated. In addition, the hydroxyl group which it carries is very notable in the sense that it is the only group of this entire cyclic undecapeptide capable of producing chemical modification. It is also possible to note already that it is in a greatly hindered stearic environment making any approach by a reagent extremely delicate.

These cyclic undecapeptides, whether they are of natural origin or are obtained by synthesis, exhibit a broad spectrum of biological activities, among which the most well-known are the imino suppressive, anti-inflammatory or anti-parasitic activities or activities making it possible to combat or decrease the resistance of cancerous tumors to other treatments. Some of these cyclic undecapeptides have been found to possess promising antiviral activities, in particular in the treatment of AIDS by inhibition replication of the human immune deficiency virus type 1 (HIV-1).

In this respect, a certain number of cyclic undecapeptides, obtained by hemisynthesis and having a structure similar to that of Cyclosporin A, but in which the nature of the amino acids in the 4-position, or in the 3- and 4-position, with respect to the MeBmt amino acid has been modified, have been described in patent application WO 00/01715 filed by the present applicant.

Recent pharmacological developments have made it possible to hope that the immuno moderating effect of cyclosporins, in particular that of Cyclosporin A, which effect is reversible and non-myelotoxic and for which few side effects have been listed, may be taken advantage of, in particular in the field of opthalmology, for local treatment, in particular, of superficial pathological conditions of the eye and of its surrounding appendages.

Included among these pathological conditions are, inter alia, dry keratoconjunctivitis, also called dry eye syndrome, Sjögren's syndrome, forms of allergic keratoconjunctivitis, in particular those resistant to corticosteroids, conjunctivitis producing mucous and synechia, herpetitic stromal keratitis, immune-related limbic keratitis and Thygeson's keratitis, and prevention of corneal transplant rejection, and as an adjuvant treatment for filtering surgery.

The cyclic undecapeptides of the cyclosporin family are highly hydrophobic in nature, which reduces all the more their solubility in water. This characteristic is related to the nature of the side chain of most of their amino acids, but also to the fact that the amine group of some of these amino acids is methylated, thus limiting the possible number of intermolecular hydrogen bond formations between the cyclic undecapeptide and, for example, an aqueous solubilizing medium.

As a result, the intravenous (i.v.) administration of these cyclosporins requires the development of very complex pharmaceutical formulations, mainly in the form of emulsions, which sometimes have precarious stability and are delicate to handle, and which are sources of adverse side effects.

By way of example, one of the preparations for i.v. infusion of Cyclosporin A, commercially available under the trademark SANDIMMUN, consists of a microemulsion using, as excipient, a polyoxyethylenated castor oil known under the trademark CREMOPHOR. This preparation is conserved in the form of a concentrate and must be diluted just before it is administered.

Due to the use of this castor oil, which is known to solubilize some of the components of synthetic materials, the manufacturer recommends using, when handling this preparation, only material made of glass or, failing this, of a synthetic material in accordance with the "standards of the European Pharmacopia for receptacles intended to contain blood", all these materials having to be free of silicone oil and of fats.

In addition, it warns the clinician that this castor oil is capable of causing anaphylactoid reactions and, as a result, recommends that intravenous administration be used only in cases where oral administration is impossible.

The development of promising uses of cyclosporins by local administration in opthalmology remains slow-moving due also to the difficulty in developing suitable pharmaceutical formulations which exhibit in particular good local tolerance and do not cause blurred vision due to the presence of viscous agents.

Thus, and by way of example, Robert et al. have recently reviewed, in J. Fr. Opthalmol., 2001, 24(5), 527, all the technical difficulties which have to be worked out due to the lypophilic nature of the pharmaceutical formulations for administering Cyclosporin A locally in opthalmology and all the problems of local tolerance which these formulations cause.

One of the conclusions which may be drawn from this review is that, to date, no formulation exists in the form of an eyewash which can be administered locally for the treatment of conditions of the eye and of its surrounding appendages. This conclusion may be broadened to the use of cyclosporin for the local treatment of conditions of the mucous membranes or of skin conditions.

Consequently, there is still a need to make available to clinicians cyclosporins, whether they are of natural or synthetic origin, or derivatives of these cyclosporins, which can be made readily administerable to a patient, in particular locally or intravenously, while avoiding the use of complex pharmaceutical formulations which have a precarious stability and which are difficult to handle, and which are sources of adverse side effects.

This need exists all the more if these cyclosporins, of natural or synthetic origins, must be applied locally to the eye or to its surrounding appendages.

One of the possibilities available to the specialist when confronted with the problem of making a hydrophobic, pharmacologically active molecule assimilable in a physiological medium is to chemically modify it in order to confer on it a hydrophilic nature.

In order to avoid altering the pharmacological properties of such a pharmacologically active molecule, this chemical modification may consist in preparing a precursor, if possible an inactive precursor, of this pharmacologically active molecule, which, once administered and under the effect of the physiological conditions existing locally in the body, will be chemically or enzymatically modified such that the pharmacologically active molecule is released, if possible, either at the site where its pharmacological action must occur, or in the blood which will transport this pharmacologically active molecule thus released to its site of action, this corresponding to the "pro-drug" concept. In the remainder of this description, the precursor in question of said pharmacologically active molecule is called "pro-drug".

It is already known practice to chemically modify the structure of Cyclosporin A for the purpose of conferring on the product obtained a hydrophilic nature.

Thus, Rothbard et al. have described, in patent application WO 01/13957, a method for improving the administration of pharmacologically active molecules and for enabling them to cross the dermis and the epithelial membranes, consisting in reversibly grafting onto these molecules a side chain consisting of fragments of a polyarginine chain. Included among the pharmacologically active molecules are molecules which are hydrophobic in nature, such as Cyclosporin A.

However, such conjugates are extremely delicate to handle and to conserve due to the fact, as is indicated in the cited application, that the pharmacologically active molecule is released as soon as the pH of the medium exceeds 7. In addition, when this pharmacologically active molecule is released, the polyarginine chain fragments are released in the body. Since they are known for their toxicity and their irritant capacity, these polyarginines would cause irritations such that use of such cyclosporin conjugates in the field of opthalmology cannot be envisioned.

Crooks et al. describe, in patent application WO 00/67801, the preparation of pro-drugs of anti-inflammatory agents such as flurbiprofen, in order to be able to administer them locally in contact with the eye, while at the same time avoiding any local irritation this time. They achieve this, for a certain number of medicinal products, by introducing oxygenated or polyoxygenated chains.

On the other hand, when wishing to subject Cyclosporin A to the same chemical modifications, they succeeded in obtaining only products which they describe as being stable, in other words, which are not cleaved to release the Cyclosporin A, whether this is in contact with human serum or in a phosphate buffer at pH 7.4.

Consequently, the aim of the present invention is to make available to the clinician pro-drugs of cyclic undecapeptides of the cyclosporin family which, firstly, can be administered within the physiological medium without having to develop complex pharmaceutical formations and, secondly, can be stored and then handled and administered without having to worry in particular about the pH conditions of the surrounding medium.

The aim of the present invention is also to make available to the clinician pro-drugs of cyclic undecapeptides of the cyclosporin family which can be administered locally in general, and in particular on the surface of the eye or on the mucous membranes and which can then release, in a suitable half-life time, the pharmacologically active cyclic undecapeptide, without local irritation.

To this effect, the present invention relates to a pro-drug consisting of a cyclic undecapeptide in which the peptide chain comprises at least one amino acid residue of general formula (I) below:

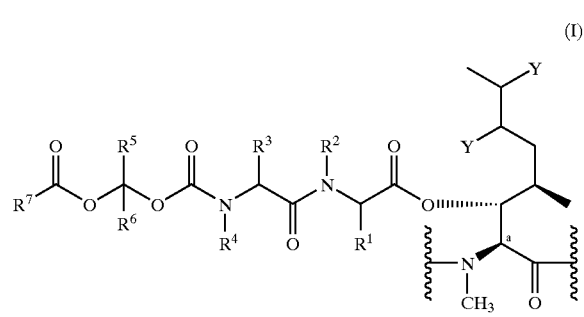

(I)

in which:

the carbon atom $C^\alpha$ constitutes one of the links of the undecapeptide ring;

the substituents Y each represent a hydrogen atom or together constitute a bond;

the substituents $R^1$ and $R^3$ represent, independently of one another, a hydrogen atom, an aralkyl group, an alkaryl group, a heteroalkyl group, a heterocyclic group, an alkylheterocyclic group, a heterocyclicalkyl group or a linear or branched alkyl group having from 1 to 6 carbon atoms, said groups being optionally substituted with at least one of the groups chosen from —COOH, —CONHR$^8$, —NHC=NH(NH$_2$), —NHC=NR$^8$(NH$_2$), —NH$_2$, —NHR$^8$, —NR$^8{}_2$, —N$^+$R$^8{}_3$, —OH, —OPO(OR$^8$)$_2$, —OPO(OH)(OR$^8$), —OPO(OH)$_2$, —OSO(OR$^8$)$_2$, —OSO(OH)(OR$^8$), —OSO(OH)$_2$, and the various salified forms of these groups, each of the substituents $R^8$ representing, independently of one another, a linear or branched alkyl group having from 1 to 6 carbon atoms;

the substituents $R^2$ and $R^4$ represent, independently of one another, a hydrogen atom, an alkaryl group, or a linear or branched alkyl group having from 1 to 6 carbon atoms;

the substituents $R^5$ and $R^6$ represent, independently of one another, a hydrogen atom, an aralkyl group, or a linear or branched alkyl group having from 1 to 6 carbon atoms; and the substituent $R^7$ represents an aralkyl group, an alkaryl group, a heteroalkyl group, a heterocyclic group, an alkylheterocyclic group, a heterocyclicalkyl group or a linear or branched alkyl group having from 1 to 6 carbon atoms, said groups being optionally substituted with at least one of the groups chosen from —COOH, —CONHR$^8$, —NHC=NH(NH$_2$), —NHC=NR$^8$(NH$_2$), —NH$_2$, —NHR$^8$, —NR$^8{}_2$, —N$^+$R$^8{}_3$, —OH, —OPO(OR$^8$)$_2$, —OPO(OH)(OR$^8$), —OPO(OH)$_2$, —OSO(OR$^8$)$_2$, —OSO(OH)(OR$^8$), —OSO(OH)$_2$, and the various salified forms of these groups, each of the substituents $R^8$ having the definition above.

When the two substituents Y together constitute a bond, said amino acid residue of general formula (I) derives from an N-methyl-(4R)-4-((E)-2-butenyl)-4-methyl-L-threonine residue in which the hydroxyl group of the threonine has been esterified in the appropriate manner, and the pharmacologically active molecule which will be released when the pro-drug is cleaved in the body will consist of a cyclic undecapeptide in which the peptide chain comprises at least one N-methyl-(4R)-4-((E)-2-butenyl)-4-methyl-L-threonine residue (MeBmt).

Similarly, when the two substituents Y each represent a hydrogen atom, said amino acid residue of general formula (I) derives from an N-methyl-(4R)-4-butyl-4-methyl-L-threonine residue in which the hydroxyl group of the threonine has been esterified in the appropriate manner, and the pharmacologically active molecule which will be released when the pro-drug is cleaved in the body will consist of a cyclic undecapeptide in which the peptide chain comprises at least one N-methyl-(4R)-4-butyl-4-methyl-L-threonine residue (Dh-MeBmt).

Preferably, in general formula (I) defining said amino acid residue, at least one of the substituents $R^1$ and $R^3$ represents an aralkyl group, an alkaryl group, a heteroalkyl group, a heterocyclic group, an alkylheterocyclic group, a heterocyclicalkyl group or a linear or branched alkyl group having from 1 to 6 carbon atoms, each of said groups being substituted with at least one of the groups chosen from —COOH, —CONHR$^8$, —NHC=NH(NH$_2$), —NHC=NR$^8$(NH$_2$), —NH$_2$, —NHR$^8$, —NR$^8{}_2$, —N$^+$R$^8{}_3$, —OH, —OPO(OR$^8$)$_2$, —OPO(OH)(OR$^8$), —OPO(OH)$_2$, —OSO(OR$^8$)$_2$, —OSO(OH)(OR$^8$), —OSO(OH)$_2$, and the various salified forms of these groups, each of the substituents $R^8$ having the definition above. These groups, acknowledged to be polar in nature, greatly improved the hydrophilic nature conferred on said pro-drug.

More preferably, said aralkyl, alkaryl, heteroalkyl, heterocyclic, alkylheterocyclic, heterocyclicalkyl or alkyl groups above are substituted with at least one of the groups chosen from —NR$^8{}_2$, —N$^+$R$^8{}_3$, —OPO(OH)$_2$ or the various salified forms of these groups, each of the substituents $R^8$ having the definition above.

More preferably, at least one of said substituents $R^1$ and $R^3$ represents a linear alkyl group having from 1 to 6 carbon atoms substituted with at least one of the groups chosen from —NR$^8{}_2$, —N$^+$R$^8{}_3$, —OPO(OH)$_2$ or the various salified forms of these groups, each of the substituents $R^8$ having the definition above.

When said substituents $R^1$ and $R^3$ represent a linear alkyl group having from 1 to 6 carbon atoms substituted with at least one of the groups chosen from —NR$^8{}_2$, —N$^+$R$^8{}_3$, —OPO(OH)$_2$ or the various salified forms of these groups, each of the substituents $R^8$ having the definition above, the corresponding amino acid residues preferably derive:

either from serine, homoserine, threonine, allothreonine, N-methylserine, N-methylthreonine or N-methylhomoserine residues, in any one of the (D) or (L) configurations, preferably the (L) confirmation, and in which the hydroxyl group has been functionalized in the appropriate manner such that the side chain of these amino acid residues carries the polar and/or solubilizing groups;

or from lysine, ornithine, arginine, N-delta-methylarginine, N-alpha-methylarginine or N-methyllysine residues, in any one of the (D) or (L) configurations, preferably the (L) configuration, and in which the respectively amine or imine group has been functionalized in the appropriate manner such that the side chain of these amino acid residues carries the polar and/or solubilizing groups.

When the substituents $R^1$, $R^2$ and/or $R^3$, and $R^4$ forming the pairs ($R^1$, $R^2$) and/or ($R^3$, $R^4$) are alkyl groups having from 1 to 6 carbon atoms, they can form, within each pair, an alkylene chain which forms, with the carbon atom and the nitrogen atom which carry them, a ring. Preferably, they constitute the side chain of a proline residue.

When the substituents $R^1$ and $R^3$ represent, independently of one another, a hydrogen atom, an aralkyl group, an alkaryl group, a heteroalkyl group, a heterocyclic group, an alkylheterocyclic group, a heterocyclicalkyl group or a linear or branched alkyl group having from 1 to 6 carbon atoms, but said groups are not substituted with at least one of the groups chosen from —COOH, —CONHR$^8$, —NHC=NH(NH$_2$), —NHC=NR$^8$(NH$_2$), —NH$_2$, —NHR$^8$, —NR$^8{}_2$, —N$^+$R$^8{}_3$, —OH, —OPO(OR$^8$)$_2$, —OPO(OH)(OR$^8$), —OPO(OH)$_2$, —OSO(OR$^8$)$_2$, —OSO(OH)(OR$^8$), —OSO(OH)$_2$, and the various salified forms of these groups, then they preferably represent the side chains of amino acid residues, in (D) or (L) configurations, preferably in the (L) configuration, or of residues of said amino acids in protected and/or activated forms and optionally having their amine group alkylated, which are usually commercially available. More preferably, said amino acid residues are chosen from the twenty amino acids usually called natural amino acids.

Also preferably, in general formula (I), the substituents $R^5$ and $R^6$ cannot simultaneously represent a hydrogen atom. Also preferably, at least one of said substituents $R^5$ and $R^6$ represents a linear or branched alkyl group having from 1 to 6 carbon atoms, and the substituent $R^7$ represents an aralkyl group or a linear or branched alkyl group having from 1 to 6 carbon atoms.

More preferably, said substituents $R^5$ and $R^6$ represent, independently of one another, a hydrogen atom or a methyl group.

Preferably, said pro-drug consists of a cyclic undecapeptide in which the peptide chain comprises a single amino acid residue of general formula (I) and thus forms an undecapeptide ring with a linear sequence of ten amino acids of general formula (II) below:

-T-U-V-W-MeLeu-Ala-X-MeLeu-Z-MeVal- (II)

in which:

T is chosen from the amino acids Ala, Abu, Nval, Val and Thr;

U is chosen from the amino acids Sar, (D)MeSer, (D)MeAla and (D)MeSer(OCOR$^9$), with $R^9$ representing a hydrogen atom, an alkaryl group, or a linear or branched alkyl group having from 1 to 6 carbon atoms;

V represents an amino acid of the general formula (N—R$^{10}$)aa, aa being chosen from the amino acids Val, Leu, Ile, Thr, Phe, Tyr and Thr and $R^{10}$ being a linear or branched alkyl group having from 1 to 6 carbon atoms;

W is chosen from the amino acids Val, Nval and Leu;

X is chosen from the amino acids (D)Ala, (D)ser, (D)Hiv, (D)Val and (D)Thr, with (D)Hiv representing a D-2-hydroxyisovaleric acid residue; and Z is chosen from the amino acids Leu and MeLeu.

Thus, when, in said amino acid residue of general formula (I), the two substituents Y each represent a hydrogen atom, the pharmacologically active molecule which will be released, during the cleavage of the pro-drug in the body, will consist of a cyclic undecapeptide of the cyclosporin family in which the peptide chain contains an N-methyl-(4R)-4-butyl-4-methyl-L-threonine residue (Dh-MeBmt).

Similarly, when, in said amino acid residue of general formula (I), the two substituents Y together constitute a bond, the pharmacologically active molecule which will be released, during the cleavage of the pro-drug in the body, will consist of a cyclic undecapeptide of the cyclosporin family in which the peptide chain comprises an N-methyl-(4R)-4-((E)-2-butenyl)-4-methyl-L-threonine (MeBmt) residue.

Preferably, these cyclic undecapeptides correspond to the cyclosporins already described in the literature as having pharmacological properties, and all having, in their peptide chain, either an N-methyl-(4R)-4-((E)-2-butenyl)-4-methyl-L-threonine (MeBmt) residue or an N-methyl-(4R)-4-butyl-4-methyl-L-threonine residue (Dh-MeBmt).

More preferably, the linear sequence of the ten remaining amino acid residues constituting, with said amino acid residue of general formula (I), said cyclic undecapeptide is chosen from the following sequences of formulae (III) to (XIV):

-Abu-Sar-MeLeu-Val-MeLeu-Ala-(D)Ala-MeLeu-MeLeu-MeVal- (III);

-Abu-(D)MeAla-EtVal-Val-MeLeu-Ala-(D)Ala-MeLeu-MeLeu-MeVal- (IV);

-Thr-Sar-MeLeu-Val-MeLeu-Ala-(D)Ala-MeLeu-MeLeu-MeVal- (V);

-Val-Sar-MeLeu-Val-MeLeu-Ala-(D)Ala-MeLeu-MeLeu-MeVal- (VI);

-Nval-Sar-MeLeu-Val-MeLeu-Ala-(D)Ala-MeLeu-MeLeu-MeVal- (VII);

-Val-(D)MeAla-MeLeu-Val-MeLeu-Ala-(D)Ala-MeLeu-MeLeu-MeVal- (VIII);

-Val-Sar-MeLeu-Val-MeLeu-Ala-(D)Val-MeLeu-Leu-MeVal- (IX);

-Val-Sar-MeLeu-Val-MeLeu-Ala-(D)Thr-MeLeu-Leu-MeVal- (X);

-Abu-(D)MeSer(OAc)-MeLeu-Val-MeLeu-Ala-(D)Ala-MeLeu-Leu-MeVal- (XI);

-Abu-Sar-MeLeu-Val-MeLeu-Ala-(D)Ser-MeLeu-MeLeu-MeVal- (XII);

-Thr-Sar-MeLeu-Leu-MeLeu-Ala-(D)-Hiv-MeLeu-Leu-MeVal- (XIII);

and -Abu-Sar-MeLeu-Val-MeLeu-Ala-(D)Val-MeLeu-Leu-MeVal- (XIV).

The pharmacologically active molecule which will be released during the cleavage of the pro-drug in the body will then be respectively one of the following cyclosporins with, as appropriate, a residue derived from threonine with a butenyl (MeBmt) or butyl (Dh-MeBmt) chain:

Cyclosporin A (CsA); (D)MeAla$^3$EtVal$^4$CsA (WO 00/01715); Cyclosporin C (CsC); Cyclosporin D (CsD); Cyclosporin G (CsG); (D)MeAla$^3$CsD; (D)Val$^8$Csl; (D)Thr$^8$Csl; (D)MeSer(Oac)$^3$CsT; (D)Ser$^8$CsA (Progress in Medicinal Chemistry, Vol 25, ed. Ellis and West, Elsevier Science Publ., Biomedical Division, 1998, pp 1–33); Thr$^2$Leu$^5$(D)Hiv$^8$Leu$^{10}$CsC (The Journal of Biological Chemistry, 1991, 266(24), 15570); (D)Val$^8$Leu$^{10}$CsA; cyclosporins A, C, D, G, I and T being described in Progress in the Chemistry of Organic Natural Products, 1986, 50, 124, the remaining cyclosporins being prepared by analogy with the method described in Helvetica Chimica Acta, 1984, 67, 502.

More preferably, the pro-drugs of the present invention have, respectively, formulae (XV) and (XVI) below:

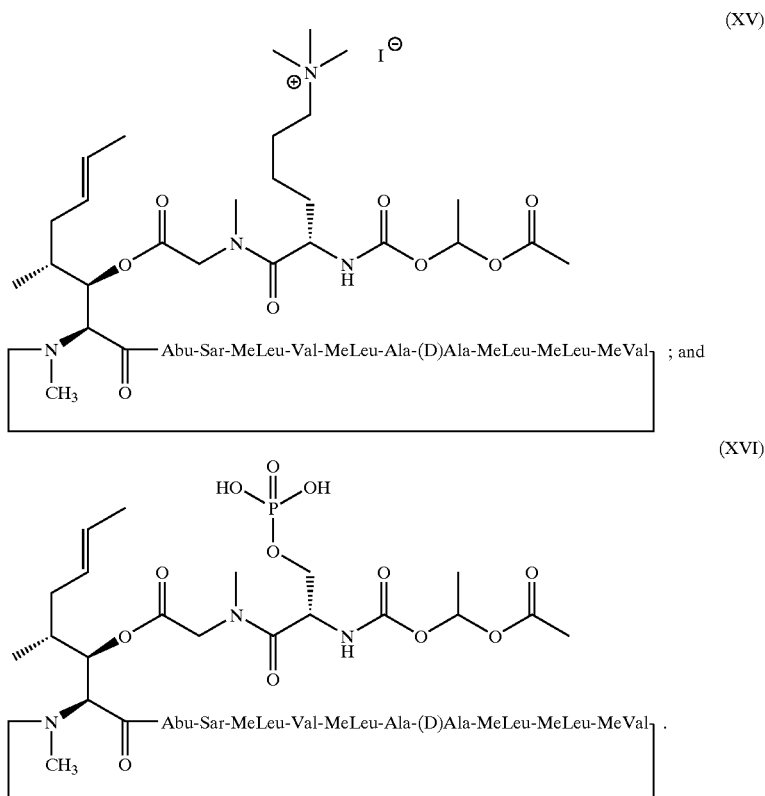

(XV) ; and (XVI).

The pro-drugs according to the present invention can be prepared by applying methods of chemical synthesis well known to the specialist in peptide chemistry, and most particularly in cyclosporin chemistry.

By virtue of an appropriate choice of the various substituents defining the amino acid residue of general formula (I), the pro-drugs according to the present invention have been found to have, notably, a greatly enhanced hydrophilic nature compared to the pharmacologically active molecule generated during the cleavage of said pro-drug. By way of example, the solubility of certain pro-drugs of the present invention, which generate Cyclosporin A after cleavage, is at least 3000 times greater than that of Cyclosporin A.

Consequently, the pro-drugs of the present invention can be easily incorporated into aqueous pharmaceutical formulation.

Also notably, the pro-drugs of the present invention are found not to be sensitive to the pH conditions usually encountered for this type of application when they are in aqueous solution.

In addition, the pro-drugs of the present invention completely fulfill their role by releasing, with a half-life time entirely suitable for a therapeutic application, the pharmacologically active molecule when they are in contact with the enzymes present in the biological humors.

The present invention also relates to the use of a pro-drug as described above, as a medicinal product.

Such a medicinal product is preferably used for the treatment of pathological conditions or physiological conditions requiring beforehand the use of a cyclosporin, in particular of all pathological conditions requiring the use of Cyclosporin A, locally or systemically by intravenous injection.

Such a medicinal product is in particular intended to allow prolonged survival of allografts of organs such as the kidney, heart, liver, pancreas, lung, small intestine or bone marrow. It may also be intended to inhibit replication of the human immunodeficiency virus type 1 (HIV-1).

In such applications, the dosage of the pro-drug of the present invention when administered systemically by intravenous injection is such that the concentration of cyclosporin generated during cleavage, for example of Cyclosporin A corresponds to the therapeutic concentrations usually recommended.

More preferably, such a medicinal product is used in the field of ophthalmology and is intended, in particular, for the treatment of pathological conditions of the eye and of its surrounding appendages.

Included among these pathological conditions are, inter alia, dry keratoconjunctivitis, also called dry eye syndrome, Sjögren's syndrome, forms of allergic keratoconjunctivitis, in particular those resistant to corticosteroids, conjunctivitis producing mucous and synechia, herpetic stromal keratitis, immune-related limbic keratitis and Thygeson's keratitis, and prevention of corneal transplant rejection, and as an adjuvant treatment for filtering surgery. More preferably, the medicinal product of the present invention is used for the treatment of dry keratoconjunctivitis.

In such applications, the dosage of the pro-drug of the present invention is such that the lachrymal concentration of cyclosporin generated during cleavage of the pro-drug, for example of Cyclosporin A, should be greater than 0.5 μg/l by local administration.

The medicinal product of the present invention can be administered topically, in particular for the local treatment of conditions of the mucous membranes or of skin conditions, or parenterally, in particular intravenously. It may also be administered orally, with the aim of improving the bioavailability of the cyclosporin, for example of the Cyclosporin A.

When the medicinal product of the present invention is administered parenterally, suitable pharmaceutical preparations may be sterile, concentrated aqueous solutions, or powders for injectable preparations.

Preferably, the medicinal product of the present invention is administered intravenously. Suitable pharmaceutical preparations for such an administration are aqueous solutions for injection or for infusion which are well known to the specialist.

More preferably, the medicinal product of the present invention is administered locally. Suitable pharmaceutical preparations for such an administration, in particular for an ophthalmic application, are eye washes, in the form of aqueous sterile solutions, ophthalmic ointments, ophthalmic gels and ophthalmic inserts.

The present invention, and also its advantageous properties, are presented in detail, without, however, being limiting, in the examples and with the aid of the drawing in which, FIG. 1 represents a curve of in vitro conversion kinetics for a pro-drug according to the invention by hydrolysis with esterases and a curve of the kinetics of appearance of Cyclosporin A;

Figure 1:
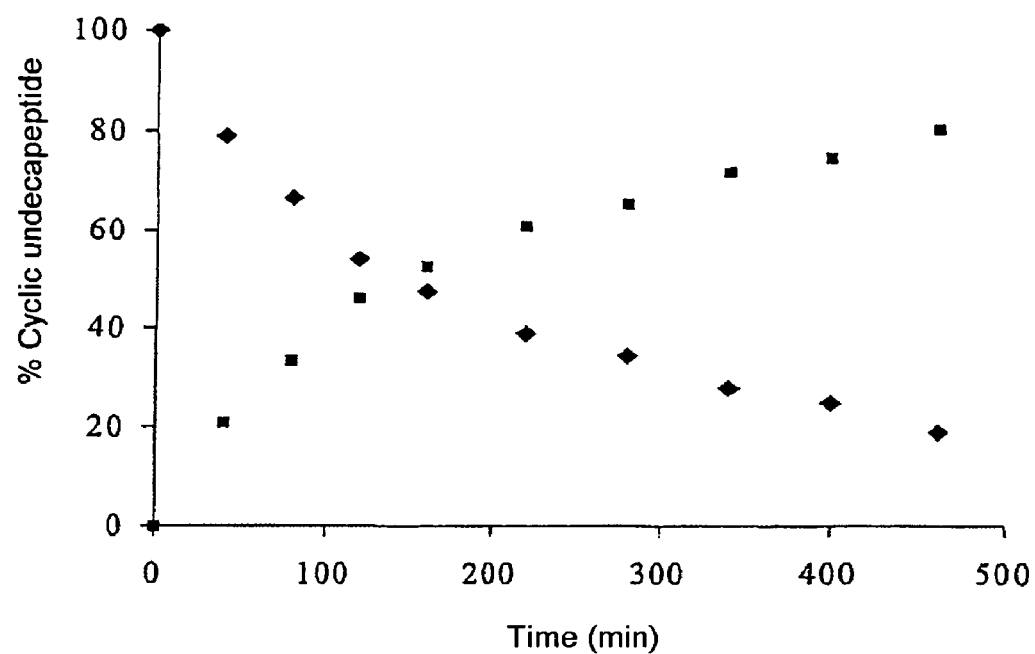

In the nomenclature used in the examples to describe the products obtained, the Cyclosporin A residue will be designated by the abbreviation—CsA, the residue of the opposite fragment being linked to the only functionalizable group of this cyclic undecapeptide, namely the hydroxyl group of the amino acid having the 1-position, N-methyl-(4R)-4-((E)-2-butenyl)-4-methyl-L-threonine (MeBmt). The structural chemical formulae of the intermediate products derived from the Cyclosporin A will represent only the amino acid residue in the 1-position with the respective side chain.

EXAMPLE 1

Preparation of the Cyclic Undecapeptide of Formula (XV)

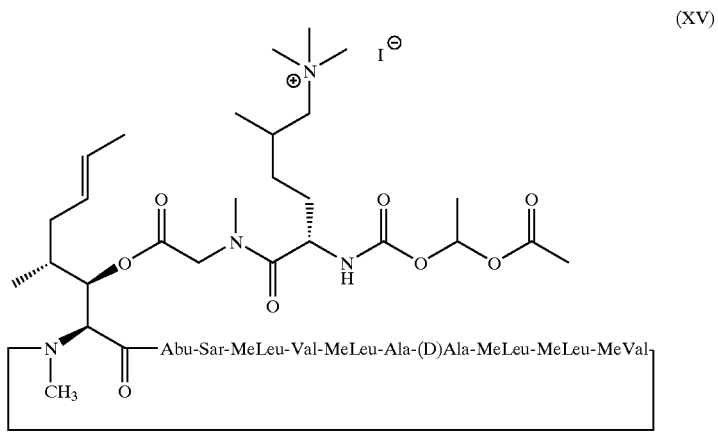

1. Preparation of MeBmt(O-Sar-Lys($N_\epsilon^+Me_3$)-COOCH($CH_3$)OCOCH$_3$))$^1$-CsA (XV)

1.1. Preparation of α-acetoxyethyl para-nitrophenyl Carbonate (2)

1.1.1. Preparation of α-chloroethyl para-nitrophenyl Carbonate (1)

2.6 ml (23.7 mmol, 1.1 eq) of α-chloroethyl chloroformate are added, at 0° C., to a solution of 3 g (21.6 mmol, 1 eq) of p-nitrophenol and 1.7 ml (21.7 mmol, 1 eq) of pyridine in 108 ml of chloroform. The reaction mixture is stirred for 30 min at 0° C. and then for 16 h at ambient temperature. The reaction mixture is extracted with water, with a 0.5% NaOH solution and then with water. The organic phase is dried over Na$_2$SO$_4$, filtered and evaporated under reduced vacuum, to give a yellow oil which gives a pure white solid (5.8 g) after crystallization from hexane.

$^1$H-NMR (400 MHz, CDCl$_3$); δ: 8.32 (d, 2H), 7.44 (d, 2H), 6.52 (q, 1H), 1.95 (s, 3H).

1.1.2. Preparation of α-acetoxyethyl para-nitrophenyl Carbonate (2)

7.8 g (24.4 mmol, 1.5 eq) of mercury acetate are added to a solution of 4 g (16.3 mmol, 1 eq) of (1) dissolved in 100 ml of acetic acid. The reaction mixture is stirred for 1 day at ambient temperature, and then an additional 1 g (3.13 mmol, 0.2 eq) of mercury acetate is added. After stirring for a further 1 day at ambient temperature, the reaction is complete. The acetic acid is evaporated off under high vacuum and the residue is taken up in ether. The organic phase is extracted with a saline solution and then dried over Na$_2$SO$_4$, filtered and evaporated under reduced vacuum, to give a yellow oil. The crude product is chromatographed on silica gel, to give a colorless oil (4.4 g).

$^1$H-NMR (400 MHz, CDCl$_3$); δ: 8.31 (d, 2H), 7.43 (d, 2H), 6.87 (q, 1H), 2.16 (s, 3H), 1.64 (s, 3H).

1.2. Preparation of α-acetoxyethoxycarbonyl-lysine (N_ε(Fmoc)) (5)

1.2.1. Preparation of the Benzyl Ester of α-acetoxyethoxycarbonyl-lysine (N_ε(Z)) (3)

500 mg (1.23 mmol, 1 eq) of H-Lys(Z)Obn.HCl are suspended in 2.5 ml of dioxane. 231 μl (1.35 mmol, 1.1 eq) of N,N-diisopropylethylamine (DIPEA) and 396 mg (1.47 mmol, 1.2 eq) of (2) are added at ambient temperature. After stirring for 1 day at ambient temperature, the reaction is complete. The dioxane is evaporated off under reduced vacuum and the residue is taken up in 20 ml of ethyl acetate. The organic phase is extracted three times with a 6% citric acid solution (20 ml), a saturated NaHCO$_3$ solution (20 ml) and a saturated NaCl solution (20 ml), dried over anhydrous Na$_2$SO$_4$ and filtered, and the solvent is evaporated off under reduced vacuum. The crude product obtained is chromatographed on silica gel, to give a clear, transparent oil (576 mg).

ESI-MS: m/z: 501.34 [M+H$^+$]; 518.28 (M+H$_2$O+H$^+$].

1.2.2. Preparation of α-acetoxyethoxycarbonyl-lysine (4)

50 mg of palladium on active charcoal are added to a solution of 509 mg (1.02 mmol) of (3) in 10 ml of ethanol. After stirring for 3 h at ambient temperature under a stream of hydrogen, the reaction is complete. The reaction mixture is filtered over celite and the filtrate is evaporated under reduced vacuum, to give the crude in the form of brownish crystals, which is used directly in the following step (254 mg).

ES-MS m/z: 276.87 [M+H$^+$].

1.2.3 Preparation of α-acetoxyethoxycarbonyl-lysine (N_ε(Fmoc)) (5)

1.11 ml of DIPEA (6.53 mmol, 1.7 eq) and 1.555 g (4.61 mmol, 1.2 eq) of Fmoc-O-Suc are added to a solution of 1.062 [lacuna] (3.84 mmol, 1 eq) of (4) dissolved in 38 ml of dioxane. After stirring for 1 h at ambient temperature, the reaction is complete. The dioxane is evaporated off under reduced vacuum and the residue is taken up in 20 ml of EtOAc. The organic phase is washed once with a 6% citric acid solution (20 ml) and a saturated NaCl solution (20 ml), dried over anhydrous Na$_2$SO$_4$ and filtered, and the solvent is evaporated off under reduced vacuum. The crude product obtained is chromatographed on silica gel, to give a white foam (1.026 g).

ES-MS m/z: 499.37 [M+H$^+$], 516.29 [M+H$_2$O+H$^+$].

1.3. Preparation of MeBmt(O-Sar-Lys((N_ε$^+$Me$_3$)-COOCH(CH$_3$)OCOCH$_3$))$^1$-CsA.I$^-$ (XV)

1.3.1. Preparation of MeBmt(O—COCH$_2$Br)$^1$-CsA (6)

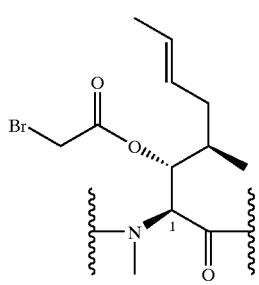

(6)

4 g (3.33 mmol, 1 eq) of dry CsA are dissolved under argon in 66 ml (0.76 mol) of bromoacetyl bromide. 2 g (16.64 mmol, 5 eq) of dimethylaminopyridine are added in small portions, and the reaction mixture is stirred at ambient temperature for 40 min. The reaction is then complete. The reaction mixture is poured, carefully and with vigorous stirring, into a mixture of hydrogen carbonate (77 g, 0.91 mol), water (500 ml) and crushed ice. The possible addition of a few further portions of NaHCO$_3$ makes it possible to bring the pH of the solution to 7–8. The separated aqueous phase is extracted twice with dichloromethane and the pooled organic phases are extracted three times with a saturated NaHCO$_3$ solution and with a saturated NaCl solution, dried over anhydrous Na$_2$SO$_4$ and filtered, and the solvent is evaporated off under reduced vacuum. The crude product obtained is chromatographed on silica gel, to give a white foam (3.2 g).

ESI-MS: m/z: 622.6 [M+2H$^+$], 673.9 [M+Na$^+$+H$^+$].

1.3.2. Preparation of MeBmt(O-Sar-H)$^1$-CsA (7)

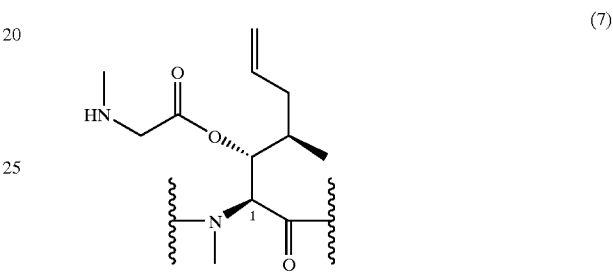

(7)

300 mg (0.23 mmol, 1 eq) of (6) are dissolved in 2.3 ml of ethanol. 95 μl (0.68 mmol, 3 eq) of triethylamine (TEA) and 31 mg (0.45 mmol, 2 eq) of additional methylammonium chloride are added at ambient temperature. After stirring for 3 days at ambient temperature, adjustment of the pH to 12 by adding TEA and addition of 15 mg (0.23 mmol, 1 eq) of methylammonium chloride, the reaction is complete after 1 hour. The ethanol is evaporated off under reduced vacuum and the residue is taken up in ethyl acetate. The organic phase is extracted with water and with a saturated NaCl solution, dried over anhydrous Na$_2$SO$_4$ and filtered, and the solvent is evaporated off under reduced vacuum. The crude product obtained is chromatographed on silica gel, to give a white foam (200 mg).

ESI-MS: m/z: 1273.7 [M+H$^+$].

1.3.3. Preparation of MeBmt(O-Sar-Lys(N_ε(FMOC-COOCH(CH$_3$)OCOCH$_3$))$^1$-CsA (8)

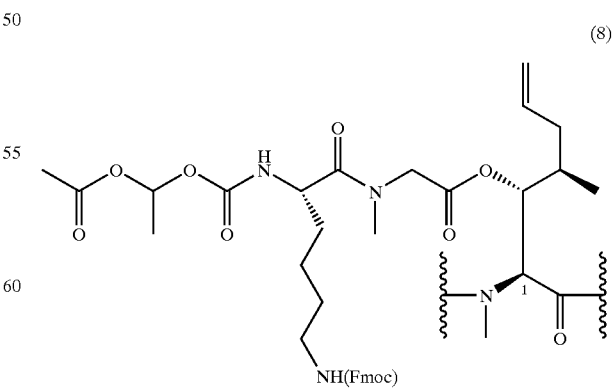

(8)

79 mg (0.06 mmol, 1 eq) of (7) are dissolved in 0.5 ml of dichloromethane (DCM) under argon. 31.6 μl (0.18 mmol, 3 eq) of DIPEA, 35 mg (0.09 mmol, 1.5 eq) of O-(7-azabenzotriazol-1-yl)-1,1,3,3-tetramethyluronium hexafluorophosphate (HATU) and 40 mg (0.08 mmol, 1.3 eq) of (5) dissolved in 0.8 ml of DCM are added successively under argon. After stirring for 3 h at ambient temperature, the reaction is complete. The DCM is evaporated off under reduced vacuum and the residue is taken up in 20 ml of EtOAc. The organic phase is washed once with a 6% citric acid solution (20 ml), a saturated $NaHCO_3$ solution (20 ml) and a saturated NaCl solution (20 ml), dried over anhydrous $Na_2SO_4$ and filtered, and the solvent is evaporated off under reduced vacuum. The crude product is chromatographed on silica gel, to give a white foam (59 mg).

ES-MS m/z: 1754.36 [M+H$^+$]; 877.86 [M+2H$^+$].

1.3.4. Preparation of MeBmt(O-Sar-Lys($N_\alpha$—COOCH($CH_3$)OCOCH$_3$))$^1$-CsA (9)

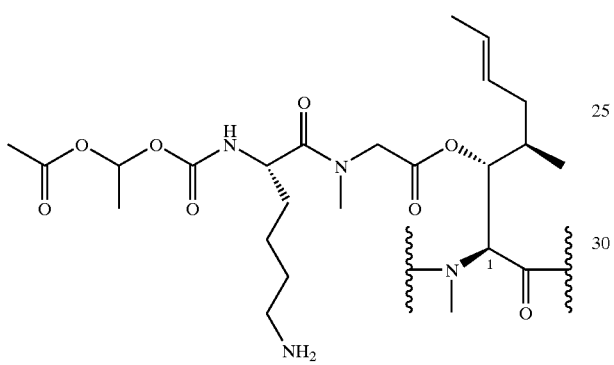

(9)

1.3.4. Preparation of MeBmt(O-Sar-Lys($N_\epsilon^+$Me$_3$)-COOCH($CH_3$)OCOCH$_3$))$^1$-CsA.I$^-$ (XV)

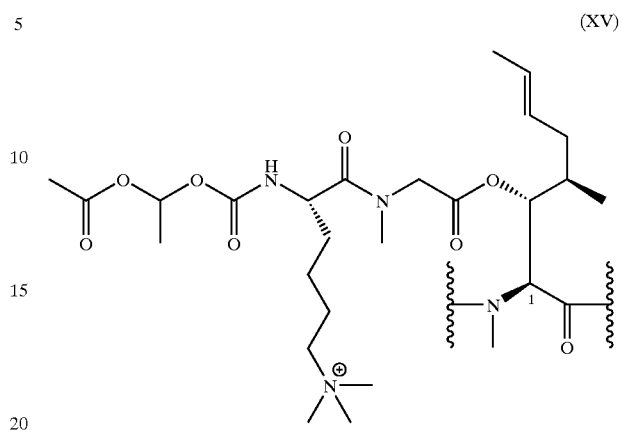

(XV)

49 mg (0.03 mmol, 1 eq) of (9) are dissolved in 640 µl of anhydrous DCM, and then 30 µl (0.48 mmol, 15 eq) of MeI are added, followed by 14 µl (0.08 mmol, 2.5 eq) of DIPEA. After stirring for 1 hour at ambient temperature, the reaction is complete. The DCM is evaporated off under reduced vacuum and the crude product is purified by semi-preparative HPLC in order to isolate the pure compound in the form of a lyophilisate (30 mg).

ES-MS m/z: 1574.37 [M+H$^+$], 787.83 [M+2H$^+$].

EXAMPLE 2

Preparation of the Cyclic Undecapeptide of Formula (XVI)

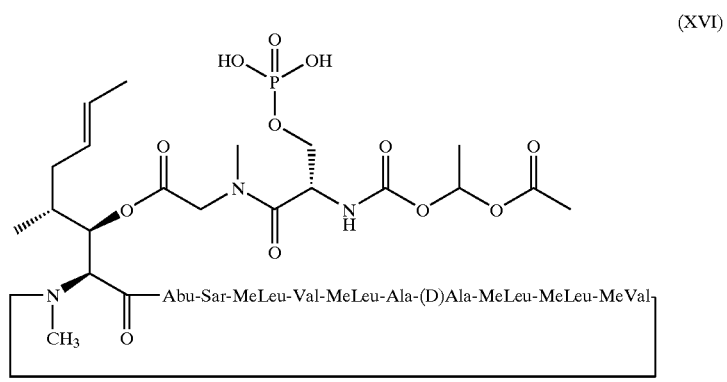

(XVI)

90 µl (0.86 mmol, 10 eq) of diethylamine are added to a solution of 150 mg (0.09 mmol, 1 eq) of (8) dissolved in 900 µl of acetonitrile. After stirring for 3 h at ambient temperature, the reaction is complete. The solvent is evaporated off under reduced vacuum and the crude product is chromatographed on silica gel, to give a white foam (52 mg).

ES-MS m/z: 1532.79 [M+H$^+$]; 766.79 [M+2H$^+$].

1. Preparation of MeBmt(O-Sar-Ser(OPO(OH$_2$))—COOCH($CH_3$)OCOCH$_3$)$^1$-CsA, (XVI)

1.1. Preparation of α-acetoxyethoxycarbonyl-serine (11)

1.1.1. Preparation of the Benzyl Ester of α-acetoxyethoxycarbonyl-serine (10)

1.4 g (6.04 mmol, 1 eq) of H-Ser-OBn.HCl are suspended in 12 ml of dioxane. 1.14 ml (6.64 mmol, 1.1 eq) of DIEA and 2.1 g (7.85 mmol, 1.3 eq) of (2) obtained according to Example 1 are added at ambient temperature. After stirring overnight at ambient temperature, the reaction is complete. The dioxane is evaporated off under reduced pressure and the residue is taken up in ethyl acetate. The organic phase is extracted three times with a 6% citric acid solution, a saturated NaHCO$_3$ solution and a saturated NaCl solution, dried over anhydrous Na$_2$SO$_4$ and filtered, and the solvent is evaporated off under reduced vacuum. The crude product obtained is chromatographed on silica gel, to give a white foam (1.7 g).

$^1$NMR (400 MHz, CDCl$_3$): δ: 7.34–7.41 (m, 5H), 6.79–6.85 (m, 1H), 5.72–5.82 (m, 1H), 5.24 (s, 2H), 4.47 (m, 1H), 3.94–4.05 (m, 2H), 2.06 and 2.08 (s, 3H), 1.49 and 1.50 (d, 3H).

1.1.2. Preparation of α-acetoxyethoxycarbonyl-serine (11)

40 mg of palladium on active charcoal are added to a solution of 400 mg (1.23 mmol) of (10) in 13 ml of ethanol. After stirring for 4 h at ambient temperature under a stream of hydrogen, the reaction is complete. The reaction mixture is filtered over celite and the filtrate is evaporated under reduced vacuum to give the crude in the form of a translucent deposit, which is directly used in the following step (328 mg).

$^1$NMR (400 MHz, CDCl$_3$): δ: 6.3–6.8 (m, 1H), 5.8–6.3 (m, 1H), 4.3–4.4 (m, 1H), 3.7–4.1 (m, 2H), 2.08 (s), 1.49 and 1.50 (d, 3H).

1.2. Preparation of MeBmt(O-Sar-Ser(OPO(OH)$_2$)—COOCH(CH$_3$)OCOCH$_3$)$^1$-CsA, (XVI)

1.2.1. Preparation of MeBmt(O-Sar-Ser(OPO(OH)$_2$)—COOCH(CH$_3$)OCOCH$_3$)$^1$-CsA, (12)

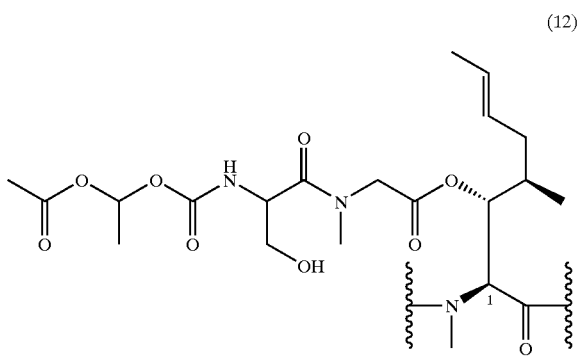

(12)

170 mg (0.13 mmol) of (7) obtained according to Example 1 are dissolved in 3 ml of dichloromethane under argon. 92 μl (0.53 mmol, 4 eq) of DIEA, 51 mg (0.26 mmol, 2 eq) of HATU and 60 mg of (11) (0.25 mmol, 2 eq) are added successively under argon. After stirring for 5 hours at ambient temperature, the reaction is complete. The dichloromethane is evaporated off under reduced vacuum and the residue is taken up in ethyl acetate. The organic phase is extracted three times with a 6% citric acid solution, a saturated NaHCO$_3$ solution and a saturated NaCl solution, dried over anhydrous Na$_2$SO$_4$ and filtered, and the solvent is evaporated off under reduced vacuum. The crude product obtained is chromatographed on silica gel, to give a white foam (143 mg).

ESI-MS: M/z: 1513.32 [M+Na$^+$], 1508.34 [M+H$_2$O+H$^+$], 1491.36 (M+H$^+$], 746.36 [M+2H$^+$]

1.2.2. Preparation of MeBmt(O-Sar-Ser(OPO(Oall)$_2$)-COOCH(CH$_3$)OCOCH$_3$)$^1$-CsA (13)

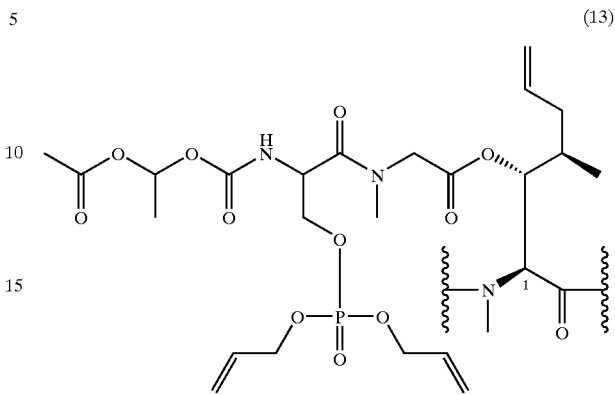

(13)

130 mg (0.09 mmol, 1 eq) of (12) are dissolved in 880 μl of anhydrous CH$_2$Cl$_2$. 20 mg (0.27 mmol, 3 eq) of 1H-tetrazole are then added, followed by 52 μl (0.17 mmol, 2 eq) of (AllO)$_2$PN(iPr)$_2$. After stirring for 4 h at ambient temperature, the reaction mixture is cooled to –60° C., 44 mg (0.17 mmol, 2 eq) of m-chloroperbenzoic acid are added, and the stirring is continued for 30 min at –60° C., 15 min at 0° C., and 45 min at ambient temperature. 0.5 ml of a 10% Na$_2$S$_2$O$_5$ solution are added, at 0° C., to the reaction medium in order to destroy the excess oxidant, and then extraction is carried out with dichloromethane. The organic phase is washed with a 10% Na$_2$S$_2$O$_5$ solution and the dichloromethane is then evaporated off under reduced vacuum. The residue is taken up in methyl tert-butyl ether and this organic phase is extracted with a 6% citric acid solution and a saturated NaCl solution, dried over anhydrous Na$_2$SO$_4$ and filtered, and the solvent is evaporated off under reduced vacuum. The crude product obtained is chromatographed on silica gel, to give a white foam (98 mg).

ESI-MS: m/z: 1651.38 [M+H$^+$], 826.35 [M+2H$^+$].

1.2.3. Preparation of MeBmt(O-Sar-Ser(OPO(OH)$_2$)—COOCH(CH$_3$)OCOCH$_3$)$^1$-CsA (XVI)

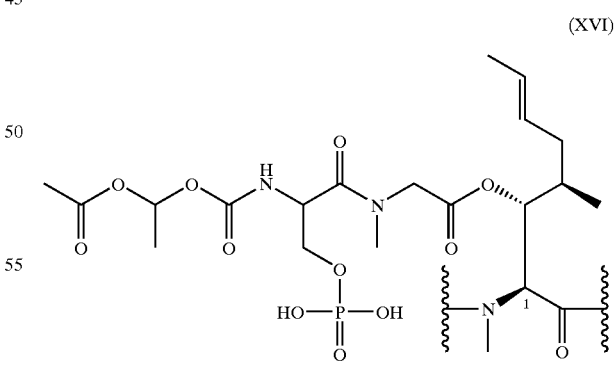

(XVI)

206 μl (1.55 mmol, 8 eq) of Me$_3$SiN$_3$ and 1.12 g (0.97 mmol, 5 eq) of (PPh$_3$)$_4$Pd° are added, under argon and at ambient temperature, to a solution of 184 mg (0.58 mmol, 3 eq) of Bu$_4$N$^+$F$^-$H$_2$O in 2 ml of CH$_2$Cl$_2$. After stirring at ambient temperature for ten minutes, 320 mg (0.19 mmol, 1 eq) of (13) are added and the reaction mixture is left to stir at ambient temperature for thirty minutes. The reaction is then complete. The reaction mixture is hydrolyzed by adding a 6% citric acid solution and the dichloromethane is evaporated off under reduced vacuum. The residue is taken up in ethyl acetate and the organic phase obtained is extracted three times with a 6% citric acid solution and a saturated NaCl solution, dried over anhydrous $Na_2SO_4$ and filtered, and the solvent is evaporated off under reduced vacuum. The crude product obtained is chromatographed on a Sep-Pack® cartridge and then on preparative HPLC, in order to isolate the pure compound in the form of a lyophilisate (342 mg).
ESI-MS: m/z: 1593.32 [M+Na$^+$], 1571.81 [M+H$^+$].

EXAMPLE 3

Physicochemical Properties of the Cyclic Undecapeptides of Formulae (XV) and (XVI)

1. Water-solubility of the Cyclic Undecapeptides of the Formula e(XV) and (XVI)

The water-solubilities were evaluated by visual examination at the ambient temperature of the laboratory, by directly dissolving a weighed amount of cyclic undecapeptide in 67 mM phosphate buffers of the Sorensen type. The values are given in Table 1.

TABLE 1

| Cyclic undecapeptide | Water-solubility at | | | |
|---|---|---|---|---|
| | pH = 5 | pH = 6 | pH = 7 | pH = 8 |
| (XV) | | | >7 mM | |
| (XVI) | >20 mM | >20 mM | >20 mM | >20 mM |

By way of indication, Cyclosporin A is described as having a maximum water-solubility of 33 µg/ml at a temperature of 20° C. and at a pH 7, which corresponds to a maximum concentration of 0.027 mM.

2. Chemical and Enzymatic Stability of the Cyclic Undecapeptide Formulae (XV) and (XVI)

A first evaluation of the chemical stability over time of the cyclic undecapeptide of formula (XV) was carried out, firstly in an isotonic solution consisting of mannitol and, secondly, in a phosphate buffer (PBS) at a pH of 7 and at temperature of 4, 20 and 37° C.

The percentages of Cyclosporin A detected are given in Table 2 below:

TABLE 2

| | 4° C. mannitol | 20° C. mannitol | 37° mannitol | 37° C. PBS |
|---|---|---|---|---|
| 30 days | 3.5% | 17.0% | 25.0% | 90.0% |
| 90 days | 5.0% | 38.0% | | |

As can be noted, at the temperature of 4° C. in a solution of mannitol, the cyclic peptide proves to be stable to respond for at least 90 days.

A second study of stabilities, both chemical and enzymatic, was carried out with the two cyclic undecapeptides of formulae (XV) and (XVI), dissolved in a 50 mM Hepes buffer at pH 7.4, at 37° C., in the presence and absence of esterases. During the incubation at 37° C., 40 µl aliquots are sampled at appropriate time periods and analyzed by HPLC and ESI-MS.

In the absence of enzyme, a chemical stability of greater than 3 days is observed for the two cyclic undecapeptides.

The results obtained during the hydrolysis in the presence of esterases have been given in FIG. 1. The curve of conversion kinetics for the cyclic undecapeptide (XVI) is represented by diamonds, while the curve of kinetics of appearance of Cyclosporin A is represented by squares. As can be noted, according to this figure, in the presence of esterases, the cyclic undecapeptide (XVI) rapidly degrades to release the Cyclosporin A. Similar observation was made for the cyclic undecapeptide (XV).

The cyclic undecapeptide (XV) and (XVI) were subjected to incubation in bovine serum at 37° C. The half-life times of conversion of the cyclic undecapeptides to Cyclosporin A were evaluated and are 3.66 and 3.50 hours, respectively.

EXAMPLE 4

Application for Intravenous Administration in the Form of an Aqueous Solution Study of Pharmacokinetics of the Cyclic Undecapeptides of Formulae (XV) and (XVI)

In order to make available to the clinician a tool which is an alternative to the pharmaceutical formulations of Cyclosporin A commonly used in the form of a microemulsion in polyoxyethylenated castor oil, which has a delicate stability, is relatively difficult to handle and induces adverse effects, pro-drugs of the present invention, in the form of simple aqueous solutions, were evaluated for the purpose of intravenous application.

Thus, the two cyclic undecapeptides (XV) and (XVI), in solution in phosphate buffer, were administered intravenously to rats at a dose equivalent to 10 mg/kg of Cyclosporin A.

As a reference, a sample of an injectable solution of Cyclosporin, commercially available on the trademark Sandimmun, was used after suitable dilution.

Blood samples were taken at regular intervals and then subjected to analysis for the purpose of assaying the Cyclosporin A.

Figure 2A:
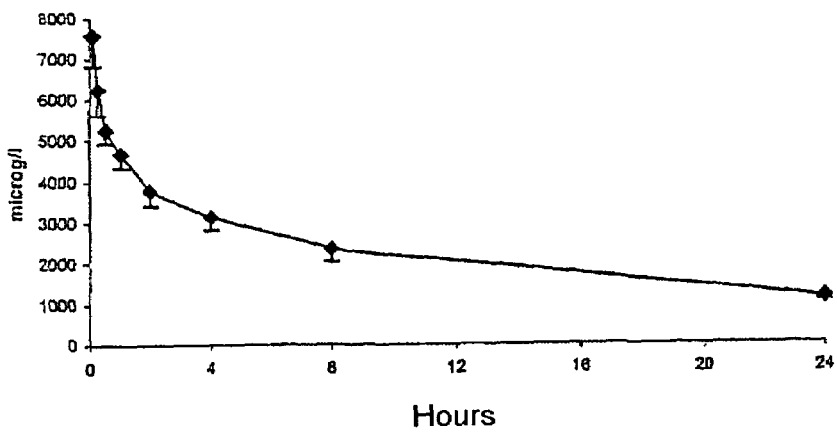
FIG. 2a represents the Cyclosporin A level in the blood after i.v. administration of Cyclosporin A in an oily form in rats.
Figure 2B:
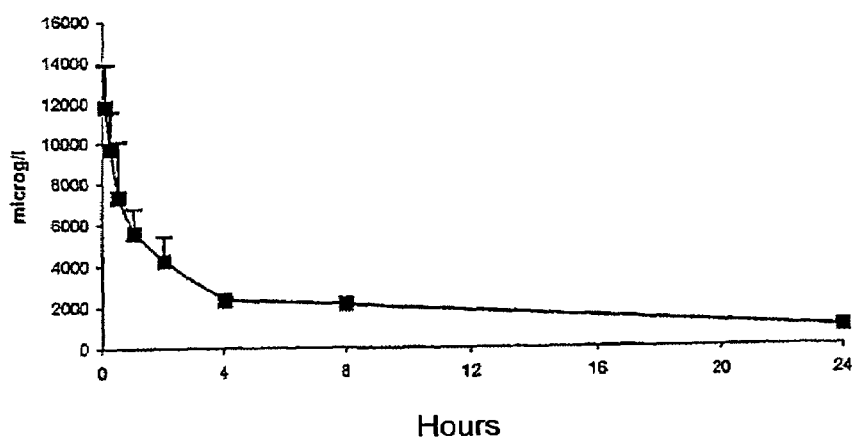
FIGS. 2b and 2c represent the Cyclosporin A level in the blood after i.v. administration of, respectively, an aqueous solution of two of the pro-drugs according to the invention in rats.
Figure 2C:
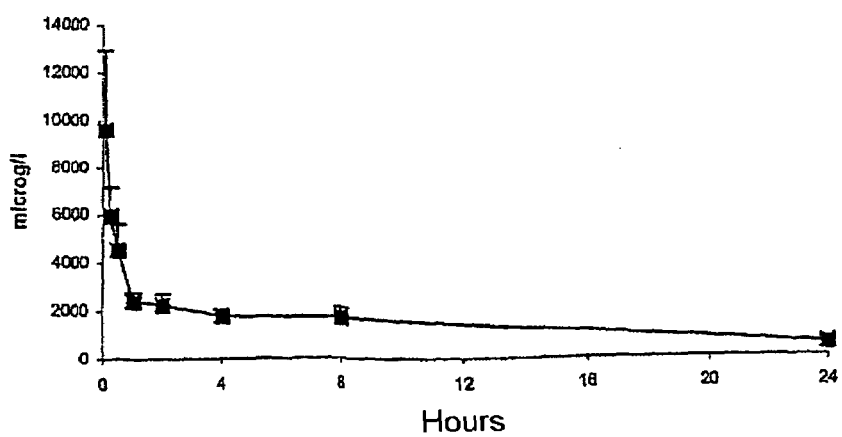

The Cyclosporin A levels in the blood after i.v. administration of Cyclosporin A have been given in FIG. 2a. Those obtained after i.v. administration of, respectively, an aqueous solution of the two pro-drugs (XV) and (XVI) are given in FIGS. 2b and 2c, respectively. The results interpreted from the curves in FIGS. 2a, 2b and 2c have been given in Table 3 below.

TABLE 3

| Undecapeptide | Cyclosporin A | (XV) | (XVI) |
|---|---|---|---|
| $AUC_{0-inf}$ µg · h · L$^{-1}$ | 69229 | 66626 | 44699 |
| CL L/h/kg | 0.14 | 0.15 | 0.22 |
| MRT h | 15.2 | 15.3 | 14.9 |
| Vss L/kg | 2.2 | 2.2 | 3.4 |
| $T1/2_1$ h | 0.31 | 0.55 | 0.20 |
| $T1/2_2$ h | 11.1 | 11.8 | 11.8 |

In this table, the abbreviations have the following meanings:
AUC: area under the curve;
CL: clearance;
MRT: mean residence time;
Vss: volume of distribution at steady state;
$T1/2_1$: initial half-life time; and
$T1/2_2$: terminal half-life time.

As can be noted from FIG. 2 and from Table 3, the pharmacokinetic parameters of the control experiment with Cyclosporin A are comparable to those reported in the literature. The area under the curve for Cyclosporin A generated during cleavage of the cyclic undecapeptide (XV) is comparable to that of the Cyclosporin A in the control experiment, whereas that of the Cyclosporin A generated during cleavage of the cyclic undecapeptide (XVI) is decreased by 25% compared to that of the Cyclosporin A of the control experiment.

The two cyclic undecapeptides (XV) and (XVI) each show a similar blood release profile for Cyclosporin A. These profiles are similar to that of the Cyclosporin A in the pharmaceutical form based on polyoxyethylenated castor oil.

From these results, it results that the pro-drugs of the present invention offer, for an equivalent Cyclosporin A release profile, the following considerable advantages compared to the existing pharmaceutical formulations of Cyclosporin A:

easy to use by simply dissolving in water; and no need to use excipients which prove to be toxic; and no need to use specific materials for handling them.

EXAMPLE 5

Application for Topical Administration to the Eye in the Form of an Aqueous Solution Study of Pharmacokinetics of the Cyclic Undecapeptide of the Formula (XV)

In order to make available to the clinician a tool for topical administration of Cyclosporin A to the eye without irritation or an unpleasant sensation being felt or without blurred vision being experienced, pro-drugs of the present invention, in the form of simple aqueous solutions were evaluated.

1. Preparation of Solutions

Isotonic aqueous solutions, containing 5% of mannitol and at pH 7.0, of the cyclic undecapeptide (XV) were prepared. The concentration of Cyclosporin A equivalent is 1% (weight/volume). The solutions were sterilized by passing them through 0.22 µm nitrocellulose filters. A reference formulation of Cyclosporin A was prepared in the form of a 1% solution in olive oil.

2. Determination of the Tolerance for the Cyclic Undecapeptide of Formula (XV)

Ocular tolerance was determined according to two methods, namely according to the modified Draize test and using a confocal laser scanning opthalmoscope.

2.1 Modified Draize Test (Acute Tolerance Test)

This evaluation was performed on six male albino rabbits. For each animal, one eye received an installation of 50 µl of the solution as described above, the other eye, not treated, playing the role of control.

The clinical evaluation of a possible irritation was performed visually by evaluating the ocular discharge, the conjuctival chemosis and the conjuctival redness according to the classification described in Table 4 below:

TABLE 4

| | | |
|---|---|---|
| Ocular discharge | Normal | 0 |
| | Slight discharge | 1 |
| | Severe discharge covering a small surface of the cornea | 2 |
| | Severe discharge covering a large part of the cornea | 3 |
| Chemosis | Normal | 0 |
| | Slight chemosis | 1 |
| | including the nictating membrane | 2 |
| | Severe chemosis with the eye partially closed | 3 |
| | Severe chemosis with the eye closed | |
| Redness | Normal blood vessels | 0 |
| | Some vessels hyperemic | 1 |
| | Diffuse redness, individual vessels not easily discernible | 2 |
| | Considerable diffuse redness | 3 |

The possible irritation was observed, in each animal, according to the rules above, at given intervals spread out over 48 hours after installation, and a total irritation index ($I_{irr}$) was calculated from the total sum of the estimated indices. The results obtained are given in Table 4 in point 2.3 below.

2.2. Confocal Laser Scanning Opthalmoscope (Test to Evaluate Subacute Toxicity Over 4 Days of Administration)

This test was carried out on the same type of animal as previously. 25 µl of a solution as described above were instilled onto the cornea of the right eye three times a day for four days, and then once on the fourth day just before observation. After the final installation, the rabbits were sedated by administering ketamine hydrochloride and xylazine. A total of 25 µl of a solution of sodium fluorescein at 0.5% by weight/volume were instilled onto the eye in order to allow selective labeling of the surfaces possibly damaged. The eye was then rinsed for one minute with a saline solution at 37° C.

Finally, the eye was observed with a confocal laser scanning opthalmoscope according to the method described by Furrer et al., J. Ocular Pharmacol., 1997, 13, 559. The opthalmoscope was coupled to an image analysis system in order to be able to reconstitute an image in three dimensions and to allow evaluation of the damaged areas.

The degree of tolerance is evaluated as a function of the percentage of corneal lesions and according to the following rule:

from 0% to 25%: good tolerance;

from 25% to 40%: acceptance tolerance;

from 40% to 60%: low tolerance; and above 60%: unacceptable tolerance.

It is noted that it is generally acknowledged that a percentage of lesions less than or equal to 5% corresponds to a usual cell mortality rate in a normal body not subjected to any treatment.

The results obtained are given in Table 5 in point 2.3 below.

2.3. Results of the Ocular Tolerance for the Cyclic Undecapeptide of Formula (XV)

TABLE 5

|  | Undecapeptide (XV) | Cyclosporin A |
|---|---|---|
| Draize, $I_{irr}$ | 1.8 | 1.9 |
| CLSO, % lesions | 7 | 23 |

From Table 5, it appears that a total irritation index 1.8 was obtained in the Draize test for the cyclic undecapeptide of the formula (XV) and that 7% of the cornea was damaged by administration of this product. These two results demonstrate very good tolerance to the cyclic undecapeptide, this tolerance being clearly improved compared to that obtained when Cyclosporin A is administered in olive oil.

For obvious reasons, the subjective improvement in the visual comfort by using an aqueous solution rather than an oily solution was not evaluated on the animal.

3. Stability of the Cyclic Undecapeptide of the Formula (XV)

Samples of the solutions described above were conserved, respectively, at 4° C. and 20° C. Analyses by HPLC were carried out regularly for 3 months. These samples were found to have good stability under such conditions.

4. Ex vivo Conversion Kinetics for the Cyclic Undecapeptide of Formula (XV)

This conversion kinetics test was carried out by incubating, at 37° C., 25 μl of a sample of the solution described above, with gentle stirring, with 8 μl of fresh rabbit tear. 2 μl samples were taken at intervals of 1, 2, 3 and 30 minutes, and were then analyzed by HPLC.

The results obtained showed that the cyclic undecapeptide of formula (XV) plays its pro-drug role from the first minute of contact with the rabbit tear, releasing the Cyclosporin A. At 3 minutes, 3% of the pro-drug has been converted, and then 4.7% after 30 minutes.

5. In vivo Conversion Kinetics for the Cyclic Undecapeptide of the Formula (XV)

This in vivo conversion kinetics test was carried out by instilling a 25 μl sample of the solution described above, in the right eye of male albino rabbits (4 kg). Tear samples were taken at intervals of 1, 2, 3, 4 and 20 minutes, and were then analyzed by HPLC.

Figure 3:
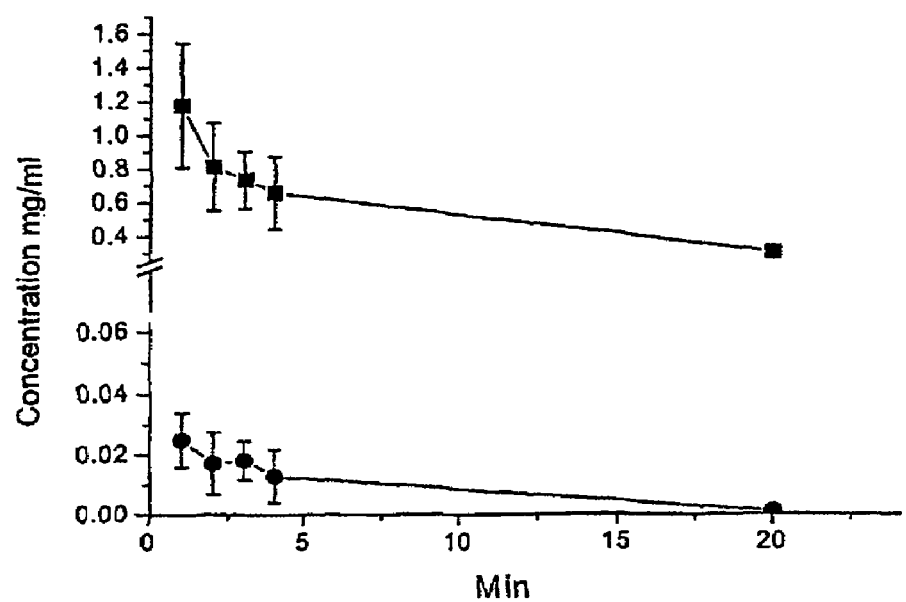
FIG. 3 represents, respectively, the concentrations over time of Cyclosporin A and of a pro-drug according to the invention, in rabbit tears.

The results obtained have been given in FIG. 3. As can be noted, this test confirms the results already obtained in the ex vivo experiment. The cyclic undecapeptide of formula (XV) (squares) clearly plays its pro-drug role from the first minute of contact with the rabbit tear, releasing the Cyclosporin A (circles), and this release continues over the following 20 minutes. At 1 minute, the concentration of Cyclosporin A in the tear is 0.025 mg/ml.

6. CONCLUSIONS

From these results, it results that the pro-drugs of the present invention offer, for topical administration to the eye, the following advantages:

ease of preparation of a pharmaceutical formulation such as an eye wash by simple dissolution in an aqueous solution without the need for using oily adjuvants;

good acute tolerance and very sub acute tolerance, greater than those obtained with a pharmaceutical formulation of cyclosporin in oily form;

good stability; and half-life time suitable for ophthalmic application.

What is claimed is:

1. A pro-drug consisting of a cyclic undecapeptide in which the peptide chain comprises at least one amino acid residue of general formula (I) below:

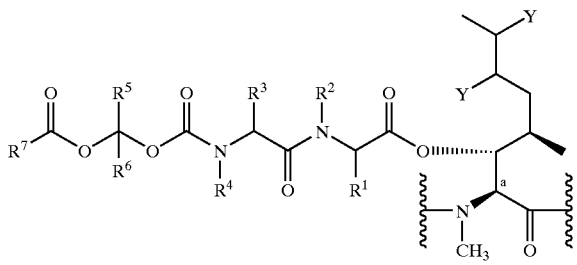

(I)

in which:

the carbon atom $C^a$ constitutes one of the links of the undecapeptide ring;

the substituents Y each represent a hydrogen atom or together constitute a bond;

the substituents $R^1$ and $R^3$ represent, independently of one another, a hydrogen atom, an aralkyl group, an alkaryl group, a heteroalkyl group, a heterocyclic group, an alkylheterocyclic group, a heterocyclic alkyl group or a linear or branched alkyl group having from 1 to 6 carbon atoms, optionally substituted with at least one of the groups chosen from —COOH, —CONHR$^8$, —NHC=NH(NH$_2$), —NHC=NR$^8$(NH$_2$), —NH$_2$, —NHR$^8$, —NR$^8{}_2$, —N$^+$R$^8{}_3$, —OH, —OPO(OR$^8$)$_2$, —OPO(OH)(OR$^8$), —OPO(OH)$_2$, —OSO(OR$^8$)$_2$, —OSO(OH)(OR$^8$), —OSO(OH)$_2$, and the various salified forms of these groups, each of the substituents R$^8$ representing, independently of one another, a linear or branched alkyl group having from 1 to 6 carbon atoms;

the substituents $R^2$ and $R^4$ represent, independently of one another a hydrogen atom, an alkaryl group, or a linear or branched alkyl group having from 1 to 6 carbon atoms;

the substituents $R^5$ and $R^6$ represent, independently of one another, a hydrogen atom, an aralkyl group, or a linear or branched alkyl group having from 1 to 6 carbon atoms; and the substituent $R^7$ represents an aralkyl group, an alkaryl group, a heteroalkyl group, a heterocyclic group, an alkylheterocyclic group, a heterocyclicalkyl group or a linear or branched alkyl group having from 1 to 6 carbon atoms, said groups being optionally substituted with at least one of the groups chosen from —COOH, —CONHR$^8$, —NHC=NH(NH$_2$), —NHC=NR$^8$(NH$_2$), —NH$_2$, —NHR$^8$, —NR$^8{}_2$, —N$^+$R$^8{}_3$, —OH, —OPO(OR$^8$)$_2$, —OPO(OH)(OR$^8$), —OPO(OH)$_2$, —OSO(OR$^8$)$_2$, —OSO(OH)(OR$^8$), —OSO(OH)$_2$, and the various salified forms of these groups.

2. The pro-drug as claimed in claim 1, characterized in that, in general formula (I) defining said amino acid residue, at least one of the substituents $R^1$ and $R^3$ represents an aralkyl group, an alkaryl group, a heteroalkyl group, a heterocyclic group, an alkylheterocyclic group, a heterocyclic alkyl group or a linear or branched alkyl group having from 1 to 6 carbon atoms, each of said groups being substituted with at least one of the groups chosen from —COOH, —CONHR$^8$, —NHC=NH(NH$_2$), —NHC=NR$^8$(NH$_2$), —NH$_2$, —NHR$^8$, —NR$^8{}_2$, —N$^+$R$^8{}_3$, —OH, —OPO(OR$^8$)$_2$, —OPO(OH)(OR$^8$), —OPO(OH)$_2$, —OSO(OR$^8$)$_2$, —OSO(OH)(OR$^8$), —OSO(OH)$_2$, and the various salified forms of these groups.

3. The pro-drug as claimed in claim 2, characterized in that said aralkyl, alkaryl, heteroalkyl, heterocyclic, alkylheterocyclic, heterocyclicalkyl or alkyl groups are substituted with at least one of the groups chosen from —NR$^8{}_2$, —N$^+$R$^8{}_3$, —OPO(OH)$_2$ or the various salified forms of these groups.

4. The pro-drug as claimed in claim 3, characterized in that at least one of said substituents R$^1$ and R$^3$ represents a linear alkyl group having from 1 to 6 carbon atoms substituted with at least one of the groups chosen from —NR$^8{}_2$, —N$^+$R$^8{}_3$, —OPO(OH)$_2$ or the various salified forms of these groups.

5. The pro-drug as claimed in claim 1, characterized in that, in general formula (I) defining said amino acid residue, the substituents R$^5$ and R$^6$ cannot simultaneously represent a hydrogen atom.

6. The pro-drug as claimed in claim 1, characterized in that, in general formula (I) defining said amino acid residue, at least one of said substituents R$^5$ and R$^6$ represents a linear or branched alkyl group having from 1 to 6 carbon atoms, and the substituent R$^7$ represents an aralkyl group or a linear or branched alkyl group having from 1 to 6 carbon atoms.

7. The pro-drug as claimed in claim 6, characterized in that said substituents R$^5$ and R$^6$ represent, independently of one another, a hydrogen atom or a methyl group.

8. The pro-drug as claimed in claim 1, characterized in that said peptide chain comprises a single amino acid residue of general formula (I) forming an undecapeptide ring with a linear sequence of ten amino acids of general formula (II) below:

-T-U-V-W-MeLeu-Ala-X-MeLeu-Z-MeVal-  (II)

in which:

T is chosen from the amino acids Ala, Abu, Nval, Val and Thr;

U is chosen from the amino acids Sar, (D)MeSer, (D)MeAla and (D)MeSer(OCOR$^9$), with R$^9$ representing a hydrogen atom, an alkaryl group, or a linear or branched alkyl group having from 1 to 6 carbon atoms;

V represents an amino acid of general formula (N—R$^{10}$) aa, aa being chosen from the amino acids Val, Leu, Ile, Thr, Phe, Tyr and Thr, and R$^{10}$ being a linear or branched alkyl group having from 1 to 6 carbon atoms;

W is chosen from the amino acids Val, Nval and Leu;

X is chosen from the amino acids (D)Ala, (D)Ser, (D)Hiv, (D)Val and (D)Thr; and

Z is chosen from the amino acids Leu and MeLeu.

9. The pro-drug as claimed in claim 8, characterized in that said linear sequence of ten amino acids is chosen from the following sequences of formulae (III) to (XIV):

-Abu-Sar-MeLeu-Val-MeLeu-Ala-(D)Ala-MeLeu-MeLeu-MeVal-  (III);

-Abu-(D)MeAla-EtVal-Val-MeLeu-Ala-(D)Ala-MeLeu-MeLeu-MeVal-  (IV);

-Thr-Sar-MeLeu-Val-MeLeu-Ala-(D)Ala-MeLeu-MeLeu-MeVal-  (V);

-Val-Sar-MeLeu-Val-MeLeu-Ala-(D)Ala-MeLeu-MeLeu-MeVal-  (VI);

-Nval-Sar-MeLeu-Val-MeLeu-Ala-(D)Ala-MeLeu-MeLeu-MeVal-  (VII);

-Val-(D)MeAla-MeLeu-Val-MeLeu-Ala-(D)Ala-MeLeu-MeLeu-MeVal-  (VIII);

-Val-Sar-MeLeu-Val-MeLeu-Ala-(D)Val-MeLeu-Leu-MeVal-  (IX);

-Val-Sar-MeLeu-Val-MeLeu-Ala-(D)Thr-MeLeu-Leu-MeVal-  (X);

-Abu-(D)MeSer(OAc)-MeLeu-Val-MeLeu-Ala-(D)Ala-MeLeu-Leu-MeVal-  (XI);

-Abu-Sar-MeLeu-Val-MeLeu-Ala-(D)Ser-MeLeu-MeLeu-MeVal-  (XII);

-Thr-Sar-MeLeu-Leu-MeLeu-Ala-(D)-Hiv-MeLeu-Leu-MeVal-  (XIII);

and

-Abu-Sar-MeLeu-Val-MeLeu-Ala-(D)-Val-MeLeu-Leu-MeVal-  (XIV).

10. The pro-drug as claimed in claim 1, having formulae (XV) below:

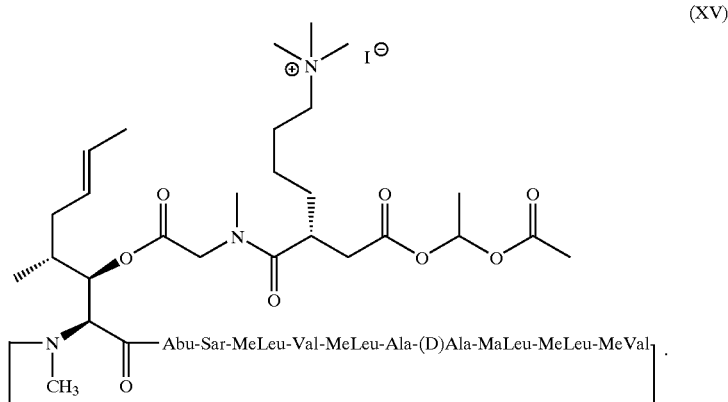

11. The pro-drug as claimed in claim 1, having formulae (XVI) below:

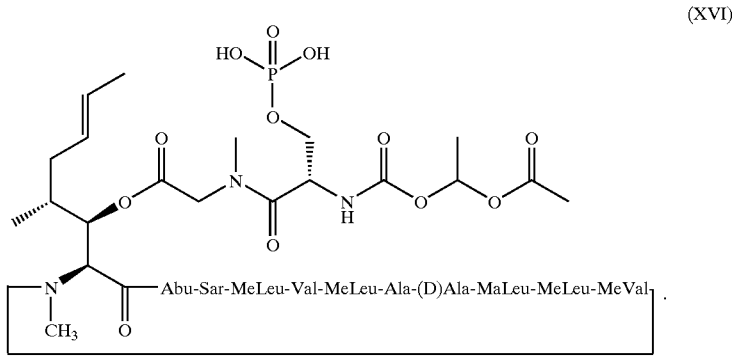

(XVI)

12. A method of treating a pathological condition of the eye in a mammal, comprising administering to a mammal in need thereof, a therapeutically effective amount of a medicinal product comprising the pro-drug of claim 1.

13. The method of claim 12, wherein the pathological condition is selected from the group consisting of: dry keratoconjunctivitis, Sjögren's syndrome, allergic keratoconjunctivitis, conjunctivitis producing mucous, synechia, herpetic stromal keratitis, immune-related keratitis and Thygeson's keratitis.

14. A method for prolonging organ allograft survival in a mammal, comprising administering to a mammal in need thereof, a therapeutically effective amount of a medicinal product comprising the pro-drug of claim 1.

15. The method of claim 14, wherein the organ allograft is selected from the group consisting of: kidney, heart, liver, pancreas, lung, small intestine, and bone marrow.

* * * * *